US008454635B2

(12) United States Patent
Paolitto et al.

(10) Patent No.: US 8,454,635 B2
(45) Date of Patent: Jun. 4, 2013

(54) SURGICAL SUTURING CLAMP

(75) Inventors: Anthony Paolitto, St. Leonard (CA);
Valerio Valentini, Montreal (CA);
Raymond Cartier, Montreal (CA)

(73) Assignee: Coroneo, Inc., Montreal, Quebec (CA)

( * ) Notice: Subject to any disclaimer, the term of this patent is extended or adjusted under 35 U.S.C. 154(b) by 1388 days.

(21) Appl. No.: 10/240,307

(22) PCT Filed: Apr. 5, 2001

(86) PCT No.: PCT/CA01/00475
§ 371 (c)(1),
(2), (4) Date: Oct. 2, 2002

(87) PCT Pub. No.: WO01/76487
PCT Pub. Date: Oct. 18, 2001

(65) Prior Publication Data
US 2003/0093091 A1  May 15, 2003

(51) Int. Cl.
*A61B 17/08* (2006.01)
*F16G 11/00* (2006.01)
(52) U.S. Cl.
USPC ........... 606/158; 606/157; 606/151; 24/129 R
(58) Field of Classification Search
USPC ................. 606/151, 153, 157, 158, 213, 216, 606/217; 24/129 R
See application file for complete search history.

(56) References Cited

U.S. PATENT DOCUMENTS

| 1,743,452 | A | * | 1/1930 | Hatch | 606/203 |
| 2,519,987 | A | * | 8/1950 | Wernette | 24/561 |
| 3,043,902 | A | * | 7/1962 | Klein | 174/146 |
| 3,357,674 | A | * | 12/1967 | Coanda et al. | 251/7 |
| 3,880,166 | A | * | 4/1975 | Fogarty | 606/158 |
| 3,910,280 | A | * | 10/1975 | Talonn | 606/203 |
| 3,993,076 | A | * | 11/1976 | Fogarty | 606/158 |
| 4,140,125 | A | | 2/1979 | Smith | |
| 4,611,593 | A | * | 9/1986 | Fogarty et al. | 606/158 |
| 4,777,950 | A | * | 10/1988 | Kees, Jr. | 606/158 |
| 5,304,188 | A | | 4/1994 | Marogil | |
| 5,473,796 | A | * | 12/1995 | Fusillo | 24/30.5 R |

(Continued)

FOREIGN PATENT DOCUMENTS

WO      9620647  A1      7/1996
WO      9725927  A1      7/1997

OTHER PUBLICATIONS

European Patent Office, International Search Report in PCT Application Serial No. PCT/CA01/00475, Jul. 4, 2001.

*Primary Examiner* — Tuan V Nguyen
(74) *Attorney, Agent, or Firm* — Wood, Herron & Evans, L.L.P.

(57) ABSTRACT

A surgical loop for constricting or ligating, partially or fully, an anatomic conduit during a surgical intervention. The surgical loop includes an elastomeric tubular body, a curved needle that is attached to one free end of the tubular body to facilitate its insertion through a body tissue containing an anatomic conduit, and a pledget which is frictionally engaged and positionable along the length of the tubular body. The pledget is frictionally engaged with a first portion of the tubular body through a closed-perimeter opening. A second portion of the tubular body is subsequently frictionally engaged or restrained with the pledget through a slot. The pledget is configured with a bias structure which maintains the slot in a biased-closed configuration to engage and restrain the second portion of tubular body.

31 Claims, 6 Drawing Sheets

U.S. PATENT DOCUMENTS 5,634,932 A * 6/1997 Schmidt ................. 606/157
5,725,542 A    3/1998 Yoon
5,984,933 A * 11/1999 Yoon .................... 606/148
6,189,186 B1 * 2/2001 Boden ................... 24/129 R

* cited by examiner

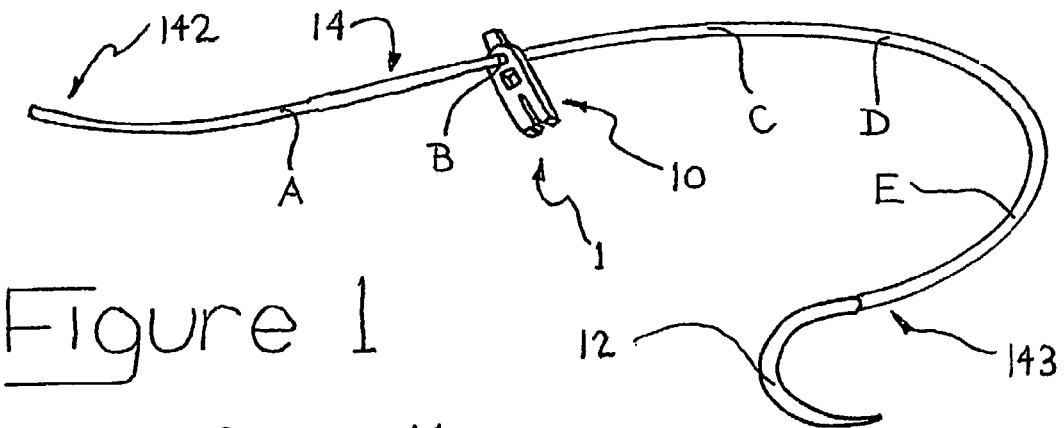
Figure 1
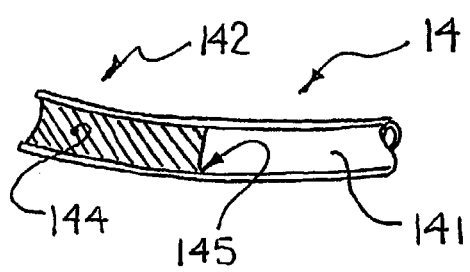
Figure 2A
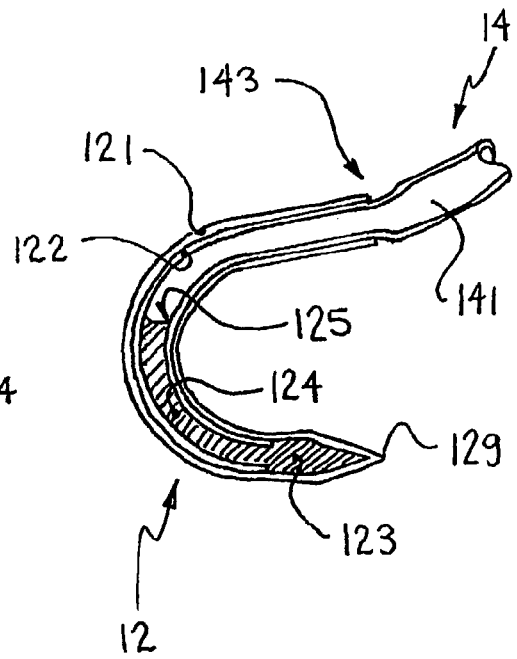
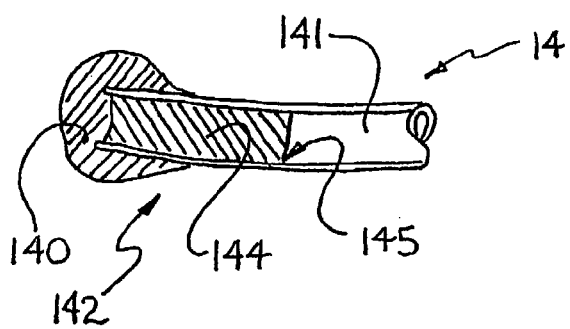
Figure 2B
Figure 2C

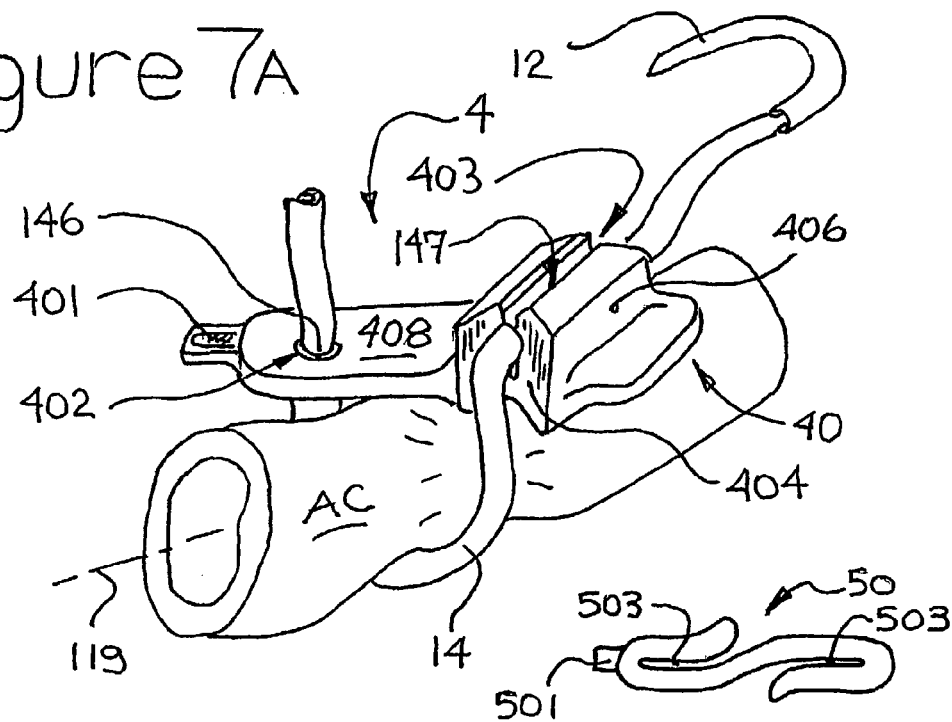
Figure 7A
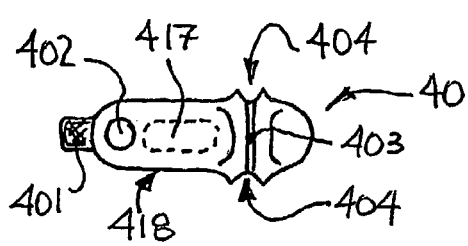
Figure 7B
Figure 7C
Figure 8A
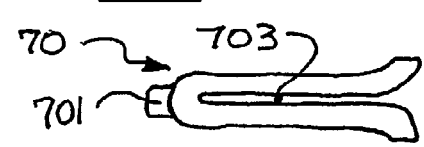
Figure 8B
Figure 8C
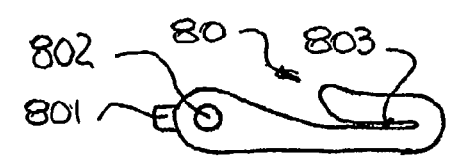
Figure 8D

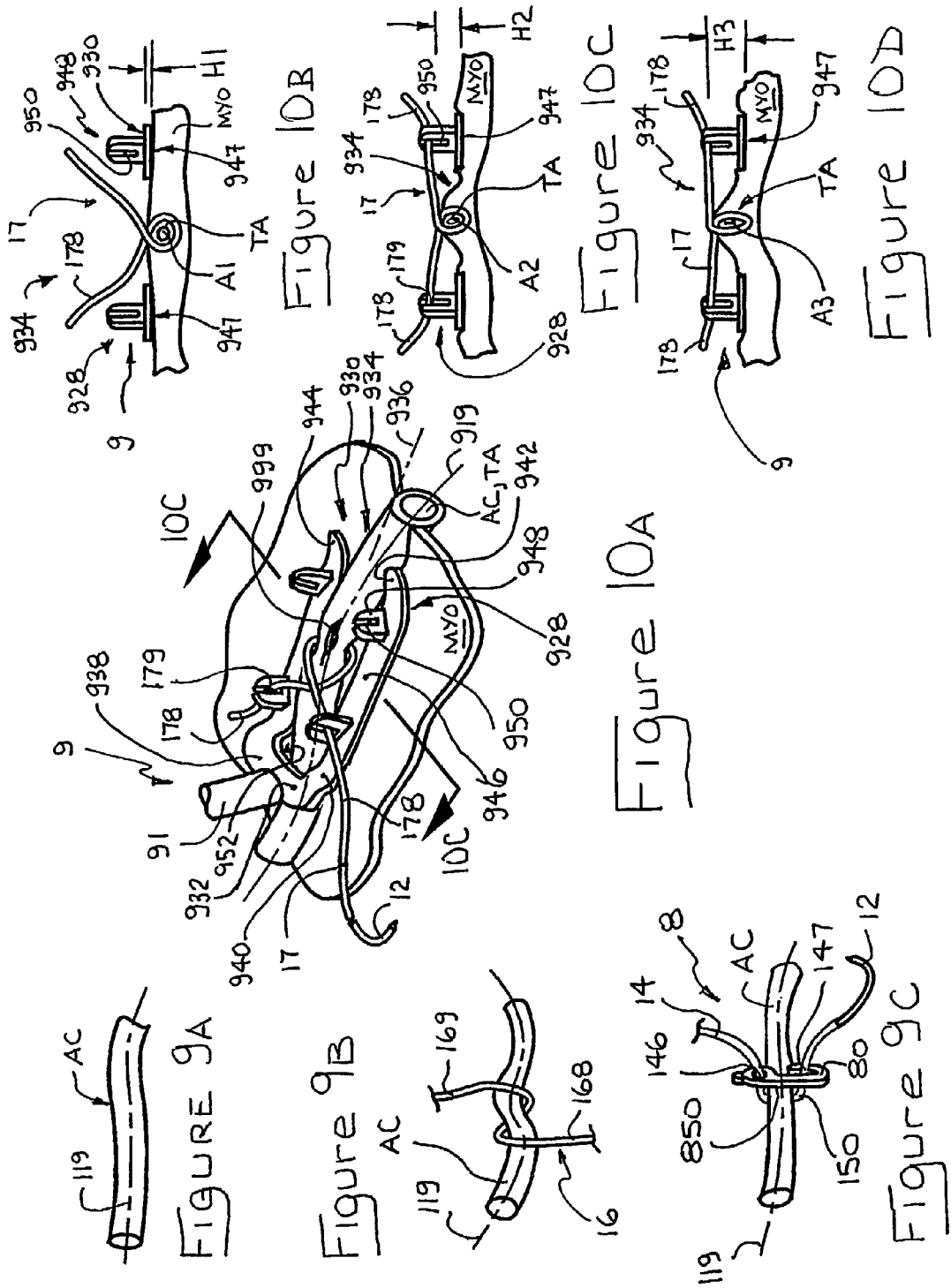

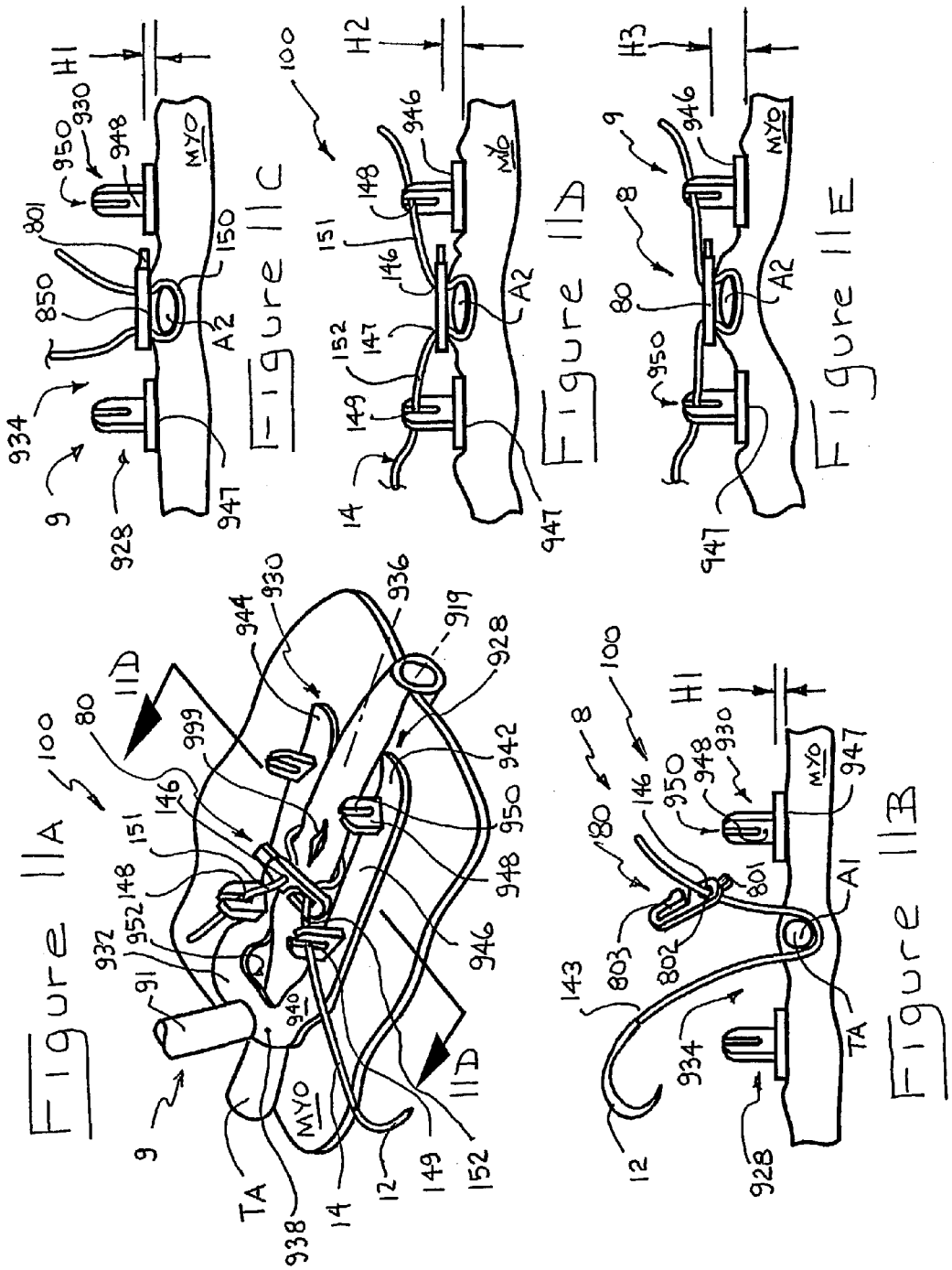

SURGICAL SUTURING CLAMP

FIELD OF THE INVENTION

The present invention relates to the field of surgical instruments and more specifically, to a surgical loop and procedure for partially or fully constricting an anatomic conduit, or displacing or restraining a body tissue.

BACKGROUND OF THE INVENTION

During the course of a surgical procedure, it is often required to displace or restrain a body tissue. This tends to facilitate surgical access to the target anatomic tissue in need of the surgical intervention, which is contained in the displaced or restrained body tissue. Alternatively, a body tissue may be displaced or restrained away from the site of a surgical intervention in which the target anatomic tissue is situated.

During many types of surgical interventions, it is also often required to constrict or ligate, either partially or fully, an anatomic conduit in order to restrict or prevent flow through said anatomic conduit, during at least a duration of the surgical intervention. For instance, during a beating heart bypass surgery procedure, an anatomic conduit such as for example a target coronary artery may be ligated to temporarily restrict or arrest blood flow through an arteriotomy incision in said target artery, while the patient's heart continues to beat. This tends to achieve a substantially bloodless surgical field during a coronary artery anastomosis surgery performed on said target artery. Other anatomic conduits include such conduits as arteries, veins, organ ducts, air passageways, or other like anatomic conduits.

Constriction or ligation of an anatomic conduit may be achieved through a hemostat or other like surgical clamp. When fragile anatomic conduits are involved, such a method of constriction or ligation tends to be traumatic. If a surgical intervention is intended on an anatomic conduit, in a region of close proximity to the site of constriction or ligation, such a method tends to yield a non-ergonomic surgical site due to the space occupied by the hemostat, or other like surgical clamp.

A non-elastic surgical suture may also be used to encircle and subsequently constrict an anatomic conduit. Pulling the loose ends of the surgical suture induces a tension in the surgical suture and results in a compressive load applied to said conduit. As such, the desired amount of constriction or ligation of anatomic conduit is achieved. The non-elastic nature of a surgical suture, and its generally thin cross-section relative to the anatomic conduit, tends to induce trauma to the said conduit. Trauma may at times result from the snaring effect, or wire-cutting effect, especially when complete ligation of an anatomic conduit is desired. Surgical sutures are generally configured with a needle at one end thereof, to facilitate their insertion through a body tissue within which an anatomic conduit is found.

Elastic ligatures have also been employed to constrict or ligate, partially or fully, anatomic conduits. The elastic quality of these elastomeric surgical loops is desirable since a certain amount of yield is provided in such surgical loops when they are engaged with anatomic tissue and pulled with the aim of ligating. As such, unlike non-elastic surgical sutures, the amount of pressure applied to an anatomic tissue, or the compression by which an anatomic conduit is constricted, tends to be more controlled. Moreover, relative to non-elastic sutures, elastomeric surgical loops will yield a certain amount if an anatomic tissue is inadvertently displaced during a surgical procedure, or will yield a certain amount if an anatomic tissue is moving or pulsating due to a physiologic function. As such, relative to non-elastic surgical sutures, there is a lower likelihood of inducing trauma to the anatomic tissue.

In certain surgeries, substantially flat elastic ligatures with solid cross section have also been employed. However, these elastic ligatures tend to dig into a body tissue or anatomic conduit if they become twisted during their deployment. This may lead to unwanted tissue trauma.

Hollow elastic surgical loops or ligatures have also been developed. With respect to solid elastic surgical loops, a hollow configuration tends to enhance the yielding potential of a surgical loop when said loop is engaged with anatomic tissue and pulled with the aim of ligating. This enhanced yielding potential tends to be accomplished without reducing the contact width of the surgical loop when it is engaged with an anatomic conduit.

Hollow elastic loops with sealed ends have also been developed with the aim of reducing the likelihood of a surgical loop twisting during its engagement and deployment with anatomic tissue. Since the ends of these hollow elastic loops are sealed to entrap air therein, collapsing of the surgical loop tends to be resisted when it is placed in contact with anatomic tissue. As such, the interior surface of the surgical loop does not easily come into contact with itself, thereby tending to reduce the likelihood of twisting said surgical loop during its deployment. Instead, this entrapped air cavity tends to facilitate the rolling of a surgical loop about its longitudinal axis as it engages with anatomic tissue. One such elastic hollow surgical loop with sealed ends is available from Quest Medical, Inc. of Allen, Tex., under brand name "Retract-O-Tape™". The Retract-O-Tape surgical loop, or vascular loop, is configured with a needle at one end thereof to facilitate its insertion through a body tissue.

The retraction of an anatomic tissue, or the constriction of a vessel contained within an anatomic tissue, is accomplished by piercing the anatomic tissue with the needle at the end of a surgical loop or suture, threading a length of surgical loop or suture through the pierced tissue, and pulling simultaneously on both resulting lengths of surgical loop or suture; that is, the length between the pierced tissue and the free end of the surgical loop or suture, and the length between the pierced tissue and the needle-bearing end of the surgical loop or suture. Once a vessel is encircled with a surgical loop or suture, pulling the two resulting lengths in a generally opposed direction induces a compressive load on the vessel contained therein. Desired vessel constriction or ligation is achieved by maintaining the tension on each of the two free lengths of the surgical loop or suture through a variety of methods. In one method, the free lengths may be held under tension by a surgical assistant. This method represents an inefficient use of the surgical assistant's time and tends to be cumbersome and non-ergonomic for the surgeon. In another method, each of the free lengths of a surgical loop may be secured to a surgical retractor, to a surgical drape, or to another part of the patient's anatomy with a surgical clamp or other like means. This tends to compromise the ergonomics of the surgical window, and the surgeon's access thereto. The situation is further aggravated when multiple surgical loops or sutures need to be secured in this manner to achieve the desired anatomic tissue retraction or vessel constriction.

Recently, with the advent of less-invasive cardiac surgery, surgical loops have been utilized to constrict or ligate coronary arteries during the course of such surgeries. For instance, in coronary artery bypass graft (CABG) surgery performed directly on a beating heart without cardio-pulmonary assistance, elastic surgical loops may be used during at least a duration of the surgical procedure to constrict or ligate a target coronary artery requiring a bypass graft. A surgical loop is generally placed around a target coronary artery, at a location upstream of the intended arteriotomy and subsequent anastomosis, thereby serving to restrict blood flow through said target artery. Another such surgical loop may be placed at a location downstream of said arteriotomy incision, tending to minimize backflow from collateral arteries. As a result, an arteriotomy and subsequent anastomosis may be performed on said target artery in a substantially bloodless surgical field while the patient's heart continues to beat.

Surgical loops may be secured in a manner as described above or may also be secured to a coronary artery stabilizer utilized to locally immobilize a portion of the beating heart surface, in the vicinity of the target coronary artery. One such coronary artery stabilizer and method of securing a surgical loop thereto is described in International Application No. PCT/CA98/00821 by Cartier and Paolitto filed Aug. 27, 1998 and entitled "Sternum Retractor for Stabilizing the Beating Heart During Coronary Artery Bypass Graft Surgery". Although, different types of coronary stabilizers exist, they tend to generally contact the surface of a beating heart with a substantially planar tissue-contact surface. Such tissue-contact surfaces are typically interrupted to define an arterial window serving to expose a target artery therebetween. For instance, in one example, the coronary stabilizer may have a substantially u-shaped contact surface. In another example, the coronary stabilizer may be comprised of two, or more, mating and demountable parts which form a substantially rectangular contact surface within which is disposed a substantially rectangular arterial window. In some types of coronary stabilizers, a surgical loop may be secured to said stabilizer through a feature such as a slotted attachment fitting, or other like means. Such attachment fittings generally protrude above the tissue-contact surface of the coronary stabilizer, and as such, a surgical loop is generally secured to said stabilizer in a location situated in height above the tissue-contact surface of said stabilizer. Encircling of the target artery with a surgical loop, and subsequently pulling and securing the ends of said surgical loop while applying a compressive force on the target artery, will tend to at least partially constrict the target artery, but also will tend to extrude through the arterial window, the portion of the myocardium tissue containing the encircled target artery. Generally in this configuration, the greater the extrusion of the myocardium through the arterial window, the greater the magnitude of the resulting constriction of the target artery contained substantially therein. In certain instances, this may lead to trauma of the coronary artery by virtue of extensive external snaring.

In a sense, encircling of an anatomic conduit with a surgical loop and subsequently pulling in a generally opposed direction, on each of the two resulting lengths of said surgical loop, applies a tourniquet effect to said conduit. In order to obtain a substantially 360 degree tourniquet, the surgical loop forms a helical winding around said conduit. As such, a shearing load is applied to the anatomic conduit by virtue of this helical winding, and by virtue of pulling on each of the two resulting lengths of surgical loop at different locations along the longitudinal axis of said conduit. This shearing action may induce a trauma to the anatomic conduit as it may cause it to twist and assume a tortuous configuration. This is especially prevalent with smaller diameter anatomic conduits, whose size approach the external cross-sectional dimension of the surgical loop.

BRIEF SUMMARY OF THE INVENTION

According to a first aspect, the present invention provides a surgical attachment device, such as a surgical loop, comprising:

an elongated wire-like member extending between a first end and a second end and having a cross-section profile adapted to vary between a free state cross-section profile and a constrained state cross-section profile;

a holding member engaged with a first portion of said wire-like member, and provided with a clamping member capable of holding a second portion of said wire-like member between at least two wire contact portions;

said wire contact portions movable, one with respect to the other, between a substantially closed configuration and an open configuration whereby at least one of said wire contact portions is resiliently biased towards said substantially closed configuration.

Such a device is of relatively simple construction, reliable and particularly easy to use. The normal position being advantageously with the wire contact portions in their closed configuration, the wire-like member remains engaged with holding member without any specific manipulation. The wire contact portions are placed in their open configuration only when the clamping member is actuated. This tends to facilitates repositioning of the engaged portion of wire-like member through the clamping member. Moreover, the risk of accidental detachment of the wire-like member from the holding member tends to be reduced since in the normal (or at rest) configuration, the wire contact portions are resiliently biased towards the substantially closed position.

Advantageously, in said substantially closed configuration, a portion of said wire-like member placed between said wire contact portions is substantially at said constrained state cross-section profile.

This closed configuration is generally utilised to hold or engage the second portion of the wire-like member, for instance once a surgical loop is disposed around a body tissue, or an anatomic conduit such as for example a coronary artery, or the like.

Advantageously, in said open configuration, a portion of said wire-like member placed between said wire contact portions is substantially at said free-state cross-sectional profile.

This open configuration is preferred during the placement or adjustment of the wire-like member with respect to the clamping member.

The holding member is advantageously further provided with an actuator adapted to move at least one of said wire contact portions of said clamping member from said substantially closed configuration to said open configuration when activated. This actuator is preferably provided with a deformable portion of said holding member.

A simple type of actuator is provided. Even though the holding member has an increased number of functional features, the number of components is kept to a minimum. The surgeon may advantageously actuate the actuator with one hand, and with the other hand place or insert a portion of wire-like member into the clamping member, or readjust the position of wire-like member within the clamping member, thus avoiding the intervention of a surgical assistant. The resiliently biased wire-contact portions automatically engage, clamp or hold the wire-like member inserted therein as the actuator is released. This effect may also be progressively provided, for instance by gradually depressing or releasing the actuator.

The holding member is advantageously unitary. A single component holding member tends to simplify construction, and facilitate operation in use. Furthermore, fewer components minimizes the likelihood of forgotten components in a patient's body after a surgical intervention is performed.

The clamping member is advantageously provided with a resilient hinge connecting said wire contact portions and disposed between said clamping member and said actuator.

In a preferred example, the wire contact portions are provided at a free end of said holding member. In a further example, the wire contact portions are provided at a substantially central portion of said-holding member, said actuator being provided at a free end thereof.

In a still further example, the surgical attachment device advantageously comprises a pair of substantially symmetrically arranged clamping members, each extending from a common hinge and each providing an actuator for the other. Such a toggle-like arrangement may provide more versatility or functionality in certain surgical interventions. It is of a simple construction and easy to use, while remaining compact.

At least one of the wire contact portions of said clamping member may advantageously cooperate with a spring-like member. The spring-like component is preferably an internally disposed or encapsulated component within the holding member, for instance covered with a polymer material or a surgery-approved material preferably similar to that of holding member. Such a construction avoids the possibility that an additional component could be damaged or lost during the surgery. The spring-like member also advantageously provides improved resiliency and is particularly resistant to cycles.

A surgical loop may be advantageously provided with a needle affixed to one end of said wire-like member. As such, this allows tubular body to be inserted through a body tissue.

A surgical loop may be advantageously provided with an enlarged ending portion configured at one end of said wire-like member. For instance, this end may be a bulb-like enlargement. In an example wherein both ends are enlarged, the holding member is thus trapped from becoming disengaged from wire-like member. The needle may also be used for this purpose. As such, an integral assembly comprising a tubular body and holding member is provided.

The wire-like member advantageously has a hollow substantially central portion. It is preferably made of elastomeric material.

In a further aspect, the invention provides a holding member for use with a surgical attachment device according to the present invention.

The invention also provides a surgical attachment device, such as a surgical loop, comprising:
  an elongated wire-like member extending between a first end and a second end and having a cross-section profile adapted to vary between a free state cross-section profile and a constrained state cross-section profile;
  a holding member engaged with a first portion of said wire-like member, and provided with a clamping member capable of holding a second portion of said wire-like member, said engagement with said first portion of wire-like member being provided by at least one attaching member, adapted to simultaneously provide:
  a sliding engagement of said wire-like member through said attaching member; and
  a restraining force acting on said wire-like member to cause said cross-section profile of said wire-like member to be altered to said constrained state cross-section profile on at least a portion of wire-like member that is in engagement with said attaching member.

The resulting engagement is of particular interest because it enables the wire-like member and the holding member to slide relative to one another when the restraining force applied by the attaching member to the engaged portion of wire-like member is overcome. The resulting friction between said attaching member and engaged portion of tubular member may advantageously be modified by varying the cross-section profile or area of the wire-like member. For instance, if the wire-like member is submitted to a tension force along its longitudinal axis, due to its elastic properties its cross-sectional area is reduced along with the cross-section profile, thus resulting in reduced friction. As such, the holding member may be positioned relatively easily along the wire-like member. Without said tension force (tubular body at rest), the tubular body resumes its free-state cross-section profile, except in the region of the engaged portion of the wire-like member with the holding member, where the attaching member provides a restraining force and the wire-like member assumes a constrained state cross-section profile and/or area. As such, a friction force between the holding member and engaged portion of wire-like member results. In this latter state, with the engaged portion of wire-like member in constrained state, the holding member is substantially held or retained but may also slide along wire-like member if a sufficient load is applied to the holding member, one that will overcome the friction force between the holding member and engaged portion of wire-like member. The resulting friction force, and ease with which holding member may slide along wire-like member, may be adjusted to a preferred level by selecting the appropriate interface dimensions, materials, and other mechanical parameters for the holding member and wire-like member. According to the present invention, a modification in the cross-sectional area also corresponds to a variation of the cross-section profile. A variation in cross-section profile, however, may or may not correspond to a change in cross-sectional area.

The invention further provides a surgical attachment device, such as a surgical loop, comprising:
  an elongated wire-like member extending between a first end and a second end, each end being provided with an abutment member;
  a holding member, slidingly engaged with said wire-like member, and movable between said abutment members;
  said holding member being provided with a clamping member capable of holding a portion of said wire-like member.

Such a surgical attachment device provides a surgical loop in which the holding member is safely maintained between the two ends of the wire-like member.

According to a further aspect, the invention further provides a holding member for a surgical attachment device comprising an elongated wire-like member, said holding member being provided with a clamping member capable of holding a portion of said wire-like member between at least two wire contact portions movable, one with respect to the other, between a substantially closed configuration and an open configuration whereby at least one of said wire contact portions is resiliently biased towards said substantially closed configuration.

Such a holding member is preferably used with a surgical attachment device such as a surgical loop, to provide a simple way of constricting or ligating an anatomic conduit and eventually readjusting said constriction or ligation during a surgery such as cardiac surgery. The holding member is preferably provided with an actuator adapted to move at least one of said wire contact portions of said clamping member from said substantially closed configuration to said open configuration when activated.

The different aspects of the invention also provide the following advantages.

The invention provides a surgical loop with a wire-like member and holding member or cooperating pledget that tends to achieve the constriction of an anatomic conduit, or anatomic tissue, through the securement of said wire-like member within said holding member or pledget. It is also advantageous that the holding member is produced as a unitary component as opposed to an assembly of components.

The holding member or pledget, and more particularly the clamping member, is adapted to be frictionally engaged with the wire-like member of a surgical loop. This tends to allow the pledget to be securely and releasably held in a desired location along the length of a surgical loop, without having to tie the pledget to the surgical loop, without having to wind the surgical loop around the pledget, or without having to glue or permanently affix the pledget to the surgical loop in a fixed position.

According to the different aspects of the invention, the amount of constriction applied to the anatomic conduit by the cooperation of a wire-like member and pledget may be easily readjusted without having to completely disengage an engaged portion of the wire-like member from its pledget and having to subsequently re-engage another portion of the wire-like member with said pledget.

Moreover, when surgical loop is used in conjunction with a coronary stabilizer used to perform surgery on a patient's heart, the invention further provides a surgical apparatus that tends to enable and maintain a desired magnitude of target artery constriction or ligation independently of the amount of extrusion of myocardium tissue within which is contained the said target artery.

The invention also provides a surgical attachment device that is able to constrict or ligate an anatomic conduit in a manner that tends to minimize the shearing action produced when an anatomic conduit is encircled with a traditional wire as previously described, thereby also tending to reduce the twisting of said conduit along its longitudinal axis.

The invention, in its several aspects, further provides a surgical loop with a wire-like member and cooperating pledget that tends to accomplish a partial constriction or full ligation of an anatomical conduit, without having to secure at least a portion of the surgical loop to a surgical retractor or other like, substantially-stable surgical support.

It also provides a surgical loop with cooperating pledget that tends to allow the readjustment of the amount of constriction or ligation of an anatomic conduit without having to completely disengage an engaged portion of wire-like member from its cooperating pledget and without having to subsequently re-engage another portion of the wire-like member with said pledget.

The invention further provides a surgical loop that tends to accomplish a partial constriction or full ligation of an anatomic conduit without inducing a twist or tortuosity to said anatomic conduit.

Finally, the present invention provides a surgical apparatus comprised of a coronary stabilizer and surgical loop with cooperating pledget that tends to maintain a desired target coronary artery constriction or ligation independently of the amount of target artery extrusion through an arterial window disposed in said coronary stabilizer.

These and other advantages of the present invention will become apparent from the description of the present invention and its preferred embodiments which follows.

BRIEF DESCRIPTION OF THE DRAWINGS

For better understanding of the present invention and to show more clearly how it may be carried into effect, reference will now be made by way of illustration and not of limitation to the accompanying drawings, which show an apparatus according to the preferred embodiments of the present invention, and in which:

FIG. 1 is a perspective view illustrating a surgical loop comprising a needle, a tubular body and cooperating pledget with aperture type bias according to a first embodiment of the present invention;

FIG. 2A is a partial cross-sectional view of the free end of the tubular body illustrated in FIG. 1;

FIG. 2B is a partial cross-sectional view of a variant of the free end of tubular body illustrated in FIG. 2A;

FIG. 2C is a partial cross-sectional view of the needle-bearing end of the tubular body illustrated in FIG. 1;

FIG. 7A is a perspective view illustrating a surgical loop comprising a tubular body and cooperating pledget with substantially non-deformable slot according to a fourth embodiment of the present invention;

FIG. 7B is a side elevational view of the pledget illustrated in FIG. 7A;

FIG. 7C is a top view of the pledget illustrated in FIG. 7A;

FIGS. 8A to 8D illustrate several variants of pledgets with substantially non-deformable slots according to a fourth embodiment of the present invention;

FIGS. 9A and 9B schematically illustrate an anatomic conduit before and after a constriction is applied from a simple surgical wire;

FIG. 9C illustrates an anatomic conduit constricted by a surgical loop according to the present invention;

FIG. 10A is a perspective view of coronary stabilizer deployed on a beating heart and comprising an array surgical wire attachment fittings;

FIGS. 10B to 10D illustrate target artery constriction achieved by a surgical wire engaged in the attachment fitting of coronary stabilizer illustrated in FIG. 10A;

FIG. 11A illustrates a perspective view of a surgical apparatus comprising a surgical loop and cooperating coronary stabilizer according to a fifth embodiment of the present invention;

FIGS. 11B to 11E illustrate target artery constriction and myocardium tissue extrusion achieved by the surgical apparatus illustrated in FIG. 11A.

DETAILED DESCRIPTION OF THE INVENTION

Figure 3A:
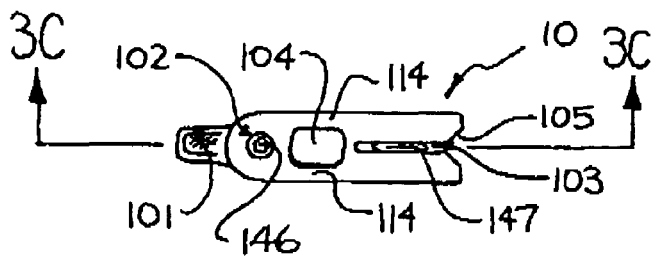
FIG. 3A is a top view of the pledget illustrated in FIG. 1 depicting the biased-closed configuration.

The features and principles of this invention can be applied, in whole or in part, to cardiac surgery, vascular surgery, or other types of surgery requiring the partial or complete constriction or ligation of an anatomic conduit, or other body tissue. The description of some of the embodiments that follow will however be illustrated in the context of cardiac surgery, and more specifically to the partial or complete constriction of a target coronary artery during beating heart bypass surgery.

In part, the embodiments of this invention may advantageously be applied, if desired, to the coronary artery stabilizer described in International Application No. PCT/CA98/00821 filed Aug. 27, 1998 in the names of Cartier and Paolitto and entitled "Sternum Retractor for Stabilizing the Beating Heart During Coronary Artery Bypass Graft Surgery", the contents of which is incorporated herein by reference. Alternatively, the embodiments of the present invention may also be applied, if desired, to other types of coronary stabilizers which are provided with a means of securing a surgical loop.

By way of a general overview and with reference to FIG. 1, a first embodiment of a surgical loop 1 is comprised of a holding member such as for example a pledget 10, a tissue-piercing means such as for example a needle 12, and a wire-like member such as for example a substantially tubular body 14.

Tubular body 14 is preferably made from an elastomeric material and is configured with a lumen 141 extending through out most of its length, between its free end 142 and its needle-engaging end 143. Free end 142 is sealed with a substantially fluid-tight seal 145 to prevent air trapped within lumen 141 from escaping. Fluid-tight seal 145 is achieved by an elastomeric plug 144, preferably made of a similar elastomeric material to the tubular body, and extending a small distance inwardly from end 142 into lumen 141 of tubular body. An example of a suitable elastomeric material is silicone elastomer, with the silicone hardening and adhering to the tubular body 14 upon curing. The silicone used is preferably of a type which self cures by reacting with moisture in the air, or cures by other like means.

Lumen 141 of hollow tubular body 14 preferably constitutes a substantial portion of the cross-section of the said tubular body, to allow the tubular body 14 to compress easily and stretch easily when placed in contact with a delicate anatomic conduit or body tissue. A lumen diameter of approximately one half, or more, of the tubular body 14 outside diameter is preferable to obtain the desired qualities of compressibility and stretchability. For instance, one example of a surgical loop 1 would have a tubular body outside diameter of 1.28 mm and a lumen diameter of 0.77 mm. Tubular body 14 may be configured in a variety of lengths, cross-sections, colors, and materials.

Tubular body 14 is preferably produced from an elastomeric material such as silicone elastomer because of its favorable biocompatibility properties. Other elastomeric materials, also approved for surgical use, may also be used. Various radiopaque substances such as barium compounds may be added to the elastomeric material composition tending to render the surgical loop 1 visible on X-ray pictures.

The opposite end of tubular body 14, needle-bearing end 143, has a needle 12 affixed to it. The attachment of a needle portion to a surgical loop is known in the prior art, and best illustrated in FIG. 2C. Needle 12 has a hollow tube portion 121 into which extends the needle-engaging portion 122 of tubular body 14. A fluid-tight seal 125 at needle-bearing end 143 is provided by way of an elastomeric plug 124 in order to maintain a pressure within lumen 141. Said plug 124 is preferably applied in a liquid state, with the elastomer curing to a solid state in a manner similar to that described for the free end 142. Elastomeric plug 124 may extend past the needle-engaging portion 122 and lumen 141 of tubular body 14 into hollow portion 123 of needle 12. As such, the elastomeric plug 124 also tends to secure needle 12 to tubular body 14. Needle 12 is preferably formed from a straight piece of hollow metal tubing such as stainless steel tubing, with the elastomeric tubular body 14 being drawn into the hollow interior of the hollow metal tubing which will form the needle 12. The hollow metal tubing may subsequently be bent, preferably in a substantial curve, and its tip swagged to form a pointed end 129. The resultant hollow tube portion 121 of needle 12 is preferably of a smaller diameter than the exterior diameter of the tubular body 14, thus allowing tubular body 14 to be compressed within said hollow tube portion 121. Compressing the engaged portion 122 of tubular body 14, especially over its elastomeric plug 124 portion, tends to secure needle 12 to tubular body 14. Once assembled, outer dimension of needle 12 at its needle-bearing end 143 is preferably flush with, or superior to, the external dimensions of tubular body 14 between ends 143, 142. This tends to facilitate the advancement of tubular body 14 through an opening created by the penetration of needle 12 through a body tissue. Because the ends 142, 143 are sealed, tubular body 14 will tend to resist collapsing and the inner surface of lumen 141 would not come easily into contact with itself, or rub against itself. As such, the surgical loop 1 will tend to resist twisting when it is pulled through a body tissue, or around an anatomic conduit, and will tend to roll about its longitudinal axis.

As mentioned, needle 12 is preferably formed in a curved configuration to facilitate its penetration through and retrieval from a body tissue. The needle is preferably of a tubular cross-section. Externally, it may also have opposing flat portions about its center axis to facilitate being grasped by a needle-holder or forceps. Pointed end 129 is preferably swagged and formed into a substantially blunt tip when used to penetrate myocardium tissue in cardiac surgery, and when surgical loop 1 is employed to constrict or ligate a coronary artery. It is also preferable to have a needle 12 with no sharp sides so as not to laterally cut body tissue while it is advanced through said tissue. Pointed end 129 may also be configured with a sharp tip.

Tubular body 14 assumes a substantially annular and circular cross-section when not exposed to any loads. This will be referred to as its free state. Stretching tubular body 14 along its longitudinal axis reduces its cross-sectional dimensions. Relieving the stretching load will tend to return the tubular body to its free state, provided the loads applied were not excessive to rupture tubular body 14, and were within the elastic limits of the tubular body material to not permanently distort tubular body 14 from its free state.

Tubular body 14 may be transversely compressed if pinched or clamped by a hemostat, by a surgical clamp, by a surgeon's fingers, or by inserting a length of tubular body 14 into a slot that is narrower than the free state dimensions of said tubular body. As such, the cross-section profile will change. This will be referred to as its constrained state. The pressure within sealed lumen 141 tends to increase when tubular body 14 is placed in a constrained state.

In this first embodiment (shown in FIG. 3A), pledget 10 is comprised of handle 101, an attaching member such as for example a closed-perimeter opening 102, a clamping member such as for example slot 103, and aperture-type bias 104. Pledget 10 is substantially elongate in shape. Pledget 10 may be produced in a variety of lengths depending on the intended surgical application, or the width of anatomic conduit it intends to constrict or occlude. In this first embodiment, bias 104 is centrally disposed between opening 102 and slot 103.

Figure 3B:
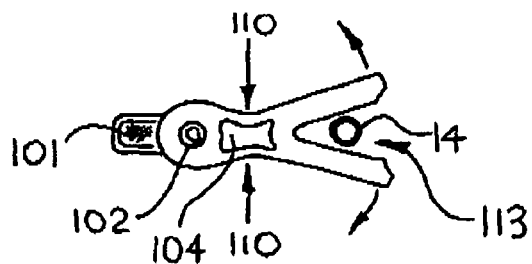
FIG. 3B is a top view of the pledget illustrated in FIG. 3A depicting the open configuration.
Figure 3C:
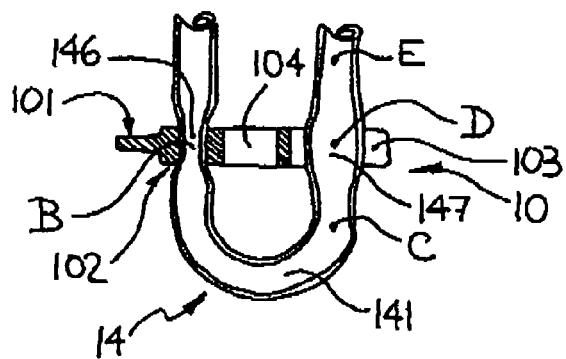
FIG. 3C is a sectional view of the pledget illustrated in FIG. 3A engaged with the tubular body of FIG. 1.

Referring to FIG. 1 and FIG. 3C, tubular body 14 is engaged with pledget 10 in a first instance through closed-perimeter opening 102. In this first embodiment, opening 102 is a substantially cylindrical opening with a diameter inferior to the free state diameter of tubular body 14. Opening 102 applies a compressive force on engaged portion 146 of tubular body 14. Engaged portion 146 is elastically deformed in directions substantially normal to its longitudinal axis. The compressive force applied by pledget 10, through opening 102, keeps said pledget frictionally engaged or restrained with tubular body 14 by virtue of the resultant friction force. Generally, the smaller the dimension of opening 102 relative to the free state diameter of tubular body 14, the greater the compressive force applied to engaged portion 146, and the greater the friction force that must be overcome to translate pledget 10 along the length of tubular body 14.

Other variants in configuration of attaching member or substantially closed-perimeter openings are also possible. For example, an opening with a tri-lobe cam profile, a triangular opening, a rectangular opening, or any other like opening may also be configured in pledget 10. At least one dimension of substantially closed-perimeter opening, the clamping dimension, applies a compressive force to engaged portion 146 of tubular body 14 in a direction substantially normal to the surfaces defining said clamping dimension. As such, the tubular body 14 is restrainingly or frictionally engaged with pledget 10 by virtue of the resultant friction force. If a larger or smaller diameter tubular body 14 is desired, the cooperating pledget opening 102 is resized in order to achieve the desired friction force. Those skilled in the art will appreciate that the desired configuration for pledget opening 102 will depend, in part, on the elasticity and stretchability of tubular body 14, the free state dimensions of tubular body 14, the wall thickness of tubular body 14, and the coefficient of friction between the mating materials of pledget 10 and tubular body 14.

Closed-perimeter openings, like opening 102, tend to keep pledget 10 integrally assembled with tubular body 14 throughout the surgical procedure. Pledget 10 is preferably provided, in a sterilized packet, already engaged with tubular body 14 (FIG. 1) through opening 102. Although the surgeon may slide pledget 10 along the length of tubular body 14, it may not be easily disengaged from tubular body 14. As such, the likelihood of loosing pledget 10, or leaving it behind in a patient, is diminished. Free end 142 of tubular body 14 may be configured with an enlargement or an abutment such as for example bulb-like shape 140 (FIG. 2B), serving to axially retain pledget 10 from disengagement at said free end. Said enlargement may be formed from a similar elastomeric material as that of elastomeric plug 144, which is applied in a liquid state and cures in a bulb-like shape over free end 142 of tubular body 14. At opposing end 143, needle 12 may serve to axially retain pledget 10 from disengagement at said needle-bearing end.

Referring again to FIG. 1, grasping tubular body 14 at one location along its length, at point A for instance, and pulling on pledget 10, tubular body 14 will progressively stretch and lengthen between point A and B. Continuing to pull in this manner will eventually overcome the friction force being exerted by pledget opening 102 on engaged portion 146 of tubular body 14, and result in pledget 10 sliding over tubular body 14 towards point C. This allows the surgeon to selectively reposition pledget 10 at a desired location along the length of tubular body 14, and at a desired distance away from the needle 12.

If tubular body 14 is grasped at a point upstream of pledget 10 and at another point downstream of pledget 10, at point A and point D for instance, and subsequently these two points are pulled apart, the tubular body external dimensions will decrease as tubular body 14 is stretched between points A and D. This includes the engaged portion 146 which will also decrease in external dimension. As such, the resultant friction force at the interface between opening 102 and engaged portion 146 will be progressively reduced as stretching is increased. The friction force is eliminated if tubular body 14 is stretched sufficiently to reduce the external dimension of engaged portion 146 below the clamping dimension of opening 102. At this point, with the stretching load maintained, pledget 10 is now easily repositioned to a desired new location along the length of tubular body 14, for instance it may be repositioned from point B to point C.

To insert a portion of tubular body 14 into a slot that is narrower than its free state dimension, one generally needs to stretch a length of tubular body 14 between two points along its length, thereby rendering thinner the external dimensions of said tubular body between said two points. Subsequently, a portion of the thinned length may be inserted into said slot. This procedure generally requires the surgeon to use two hands to stretch the tubular body 14, or to use the aid of a surgical assistant.

Bias 104 serves to facilitate the insertion of a portion of tubular body 14, in its free state, into a slot that is narrower than its free state dimension, by entraining a deformation in said slot that eliminates the need to have to stretch and render thinner the tubular body portion to be inserted. Bias 104 serves to maintain slot 103 in its biased-closed configuration (FIG. 3A). That is, when bias 104 is not overridden, the surfaces defining slot 103 will be maintained at a required width to exert a desired compression and resultant friction force on a tubular body portion 147 that is inserted there within. When the bias is not overridden, the pledget assumes its normal, non-actuated biased-closed configuration. Bias 104 may be overridden by applying a compression force along arrows 110 to actuator side rails 114. As a result, slot 103 will be deformed to its open configuration 113 (FIG. 3B), and remain in this configuration for as long as compression force 110 is applied. In this first embodiment, open slot configuration 113 is substantially V-shaped. The surfaces that define slot width 103 in its biased-closed configuration, are spread apart in a hinge-like manner to their open configuration where they are capable of receiving a portion of tubular body 14 in its free state. Compression force 110 is preferably applied with a forceps, or other like surgical implement. Therefore, the surgeon may override bias 104 by applying a compression force to actuator side rails 114 with one hand, and subsequently insert a portion of tubular body 14 into open slot 113 with the other hand, without having to stretch and render thinner said portion of tubular body 14 prior to its insertion. Relieving the compression force 110 will return open slot 113 to its biased-closed configuration 103, thereby frictionally engaging a portion of tubular body 14 within pledget 10. Bias 104 is generally an aperture, preferably extending through entire thickness of pledget 10 just as the slot 103 extends through entire thickness. The longitudinal axis of bias 104 is substantially parallel to longitudinal axis of opening 102. Alternatively, bias 104 may extend only partially through the thickness of pledget 10. Alternatively, bias 104 may be a substantial cavity contained within body of pledget 10 and centrally disposed between opening 102 and slot 103. In this first embodiment, slot 103 is substantially deformable from a biased-closed configuration to an open configuration.

Alternatively, slot 103 may be defined by one geometric surface. Said geometric surface will provide two or more wire-contacting portions acting substantially in opposition to exert a desired compression and resultant friction force on a tubular body portion 147 that is inserted therein.

Generally, after a length of tubular body 14 between needle 12 and point B is inserted and threaded through a body tissue, pledget-engaged portion 147 of tubular body 14 is inserted into slot 103. If said body tissue contains an anatomic conduit, said conduit may also be constricted and ligated depending on the resultant length of tubular body 14 between engaged portions 146 and 147. In the biased-closed configuration, width of slot 103 acts as the clamping dimension which maintains a compression force or pinching load on portion 147 of tubular body 14. The force required to overcome friction between slot 103 and engaged portion 147, and cause tubular body 14 to slip through said slot, is generally greater than the force required to maintain a desired constriction of the anatomic conduit which is partially encircled by the length of tubular body 14 between engaged portions 146 and 147, and the tissue contacting portion of pledget 10. In a preferred example, as illustrated in FIG. 3A, in its biased-closed configuration, the clamping width of slot 103 will sufficiently compress pledget-engaged portion 147 to at least bring the inner surface of lumen 141 into contact with itself.

Referring to FIG. 3C, once an anatomic conduit is substantially encircled by a portion of tubular body 14 between point B and D, pulling on tubular body 14 at point E, for instance, while holding pledget 10 through handle 101 will allow a length of tubular body 14 to slide through slot 103, from point D to point C for instance. Said length of tubular body 14 slides through slot 103 in a similar manner as a length of tubular body 14 through opening 102, as discussed above. This allows the surgeon to alter the constriction imposed on an anatomic conduit, without having to disengage and subsequently re-engage tubular body 14 into slot 103. Alternatively, bias 104 may also be compressed thereby opening slot 103 to its open configuration 113, and allowing tubular body 14 to be disengaged at point D and re-engaged at point C, for instance. Chamfers 105 may also be configured by the two opposing leading edges of slot 103, in order to facilitate insertion of a portion of tubular body 14 into slot 103, when bias 104 is not activated to place slot 103 in its open configuration 113.

Pledget 10 is preferably manufactured from an injection-molded, resilient polymeric material approved for surgical use. Said material is able to withstand a compression force applied at actuator side rails 114 of bias 104. Said material, when in a configuration such as for example the design of bias 104, is also able to elastically deform from its biased-closed configuration 103 to its open configuration 113, and subsequently resume its biased-closed configuration once said compression force is relieved. Said material, is also preferable capable of withstanding repeated cycles from biased-closed 103 to open configuration 113.

Handle 101 preferably extends outward from body of pledget 10, in the vicinity of opening 102. In a manner described above, handle 101 serves to allow the surgeon to reposition pledget 10 in a desired location along a length of tubular body 14. Handle 101 may be textured to improve grasping contact with tips of a surgical forceps, or other like surgical implement.

Figure 4A:
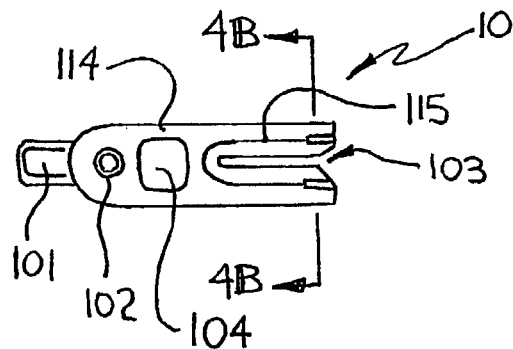
FIG. 4A is top view of a variant of the pledget illustrated in FIG. 3A depicting an elastic spring member.
Figure 4B:
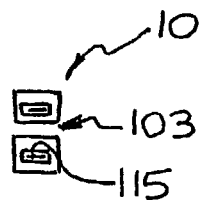
FIG. 4B is a sectional view of the pledget illustrated in FIG. 4A.

In a variant of this first embodiment (FIG. 4A), an elastic or resilient spring member 115 may be inserted within pledget 10 to tend to improve the resiliency of pledget slot 103 towards its biased-closed configuration. Spring 115 is offset from either side of slot 103, and extends over at least a portion of the length of said slot. Spring 115 is preferably encapsulated entirely within the body of pledget 10. A metallic spring is preferably used, which may be inserted into a pledget-forming mold, prior to the injection molding of pledget 10. Alternatively, a shape memory alloy such as Nitinol in its austenitic state may also be used for the material of spring 115, because of its superelastic properties. Other spring materials may also be possible without departing from the spirit of the present invention.

Figure 3D:
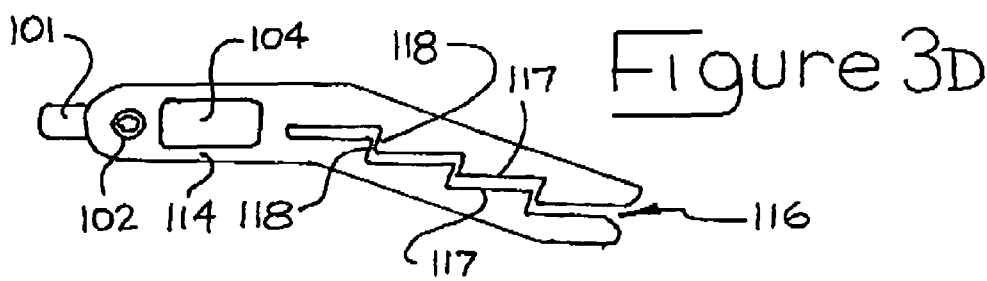
FIG. 3D is a top view of a variant of the pledget illustrated in FIG. 3A depicting a slot with saw-tooth like configuration.

In another variant of this first embodiment, at least a portion of slot 103 which engages with tubular body 14 may be textured in order to tend to encourage said tubular body to remain in engagement with said slot. Such a texture serves to enhance friction between slot 103 and the engaged portion 147 of tubular body 14. Texture may be comprised of a multitude of raised peaks, a plurality of tiny ridges and depressions, an adhesive type coating, or other like textures. Alternatively, as illustrated in FIG. 3D, a slot 116 may be configured with a saw-tooth like configuration, which tends to prevent engaged portion 147 of tubular body 14 from being laterally displaced out of engagement from said slot. The clamping dimension is provided across opposing faces 117. Faces 118 tend to be in closer proximity than faces 117 when slot 116 is in biased-closed configuration, with a portion of tubular body 14 engaged therewithin. This tends to prevent engaged portion 147 from coming out of engagement from said slot. A single saw-tooth configuration, with one slot 116 and two opposing faces 117 and two opposing faces 118, is also possible. As such, a compression force applied to side rails 114 will entrain slot 116 to assume its open configuration, thereby allowing a portion of tubular body 14 to more easily pass through opposing faces 118, and attain its placement within opposing faces 117. Once the compression force on side rails 114 is released, opposing faces 117 apply a compressive force on the engaged portion 147 of tubular body 14. Opposing faces 118 tend to prevent engaged portion 147 from coming out of engagement from said slot when pledget is in its closed configuration and no compression force is applied on side rails 114.

Figure 5A:
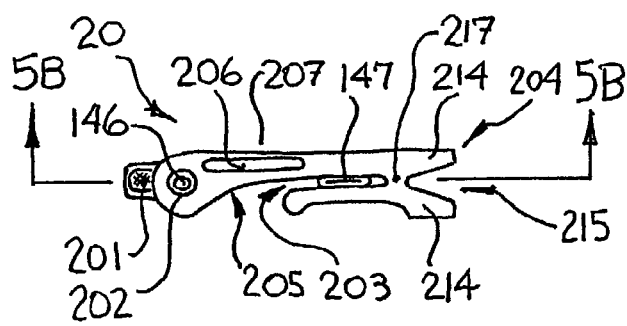
FIG. 5A is a top view illustrating a surgical loop comprising a tubular body and cooperating pledget with beam-type bias according to a second embodiment of the present invention.
Figure 5B:
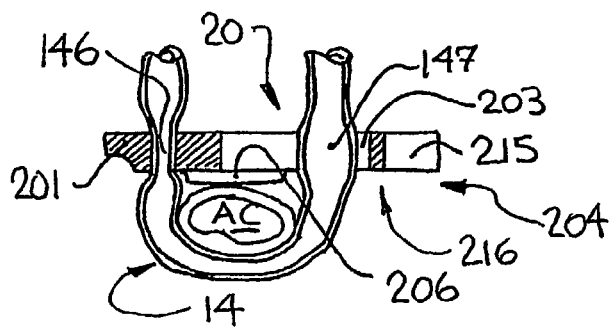
FIG. 5B is a sectional view of the surgical loop illustrated in FIG. 5A depicting its engagement with an anatomic conduit.

With reference to FIGS. 5A and 5B, a second embodiment of a surgical loop 2 is comprised of a pledget 20, a needle 12, and a substantially tubular body 14. Needle 12 and tubular body 14 are the same as those described in the first embodiment. In this second embodiment, pledget 20 is comprised of a handle 201, a closed-perimeter opening 202, a slot 203, and beam-type bias 204.

Pledget 20 is substantially elongate in shape, with bias 204 configured outboard from slot 203. Unlike pledget 10, pledget 20 tends to provide a substantially uninterrupted portion 207 of pledget body between opening 202 and slot 203. As such, uninterrupted portion 207 spans in a substantially transverse fashion over an anatomic conduit or other body tissue when surgical loop 2 is fully deployed and engaged portions 146, 147 are engaged in closed-perimeter opening 202 and slot 203, respectively (FIG. 5B). When surgical loop 2 is fully deployed, uninterrupted portion 207 cooperates with the length of tubular body 14 between engaged portions 146, 147 to constrict or ligate an anatomic conduit that is encircled or looped by said length of tubular body and said uninterrupted portion of pledget. An external occluder such as for example protruding ridge 206 may be provided to tend to enhance the constriction or ligation of an anatomic conduit when surgical loop 2 is fully deployed. Protruding ridge 206 extends away from contact surface 216 and assumes a substantially perpendicular orientation relative to the longitudinal axis of anatomic conduit when surgical loop 2 is fully deployed. Protruding ridge 206 spans along the substantially lengthwise dimension of elongate pledget 20, over at least a portion of uninterrupted pledget portion 207 between opening 202 and slot 203. Alternatively, a series of smaller ridges, a plurality of diamond shape protrusions, a series of pedestals, or other like features may be provided, extending away from contact surface 216, to tend to enhance the constriction or ligation of an anatomic conduit when surgical loop 2 is fully deployed.

Beam-type bias 204 is configured with a flexible beam member 217 from which extend, in a generally outboard direction, two end rails 214. Flexible beam member 217 defines the end of slot 203 in the inboard direction of pledget 20, and the end of v-notch opening 215 in the outboard direction of pledget 20. Bias 204 tends to maintain slot 203 in a biased-closed configuration. Slot 203 is deformed to its open configuration when bias 204 is overridden through the application of a compressive force across end rails 214. As such, the surfaces defining slot 203 are spread apart, in a hinge-like manner, while actuator end rails 214 are brought closer together in a manner that closes v-notch opening 215. Slot 203 will open progressively, up until end rails 214 come into contact with one another, and v-notch opening 215 is substantially closed. As such, v-notch opening 215 may be sized to allow the desired spreading apart of surfaces that define slot 203, such that a portion of tubular body 14 may be inserted there within in its free state. V-notch opening 215 may be sized to limit the amount of deformation exerted on pledget 20 by the application of said compressive force, such that the material properties of pledget 20 remain resilient and tend to return pledget 20 to its biased-closed configuration.

Pledget 20 is provided with access ramp 205 which tends to facilitate the insertion of a portion of tubular body 14 within slot 203. FIG. 5B illustrates a surgical loop 2 in its fully deployed state, serving to constrict an anatomic conduit, labelled AC. To engage a portion of tubular body 14 into slot 203, the surgeon may grasp pledget 20 with a forceps, or like surgical implement, across end rails 214 while applying a compressive force to said rails to override bias 204. The surgeon may then grasp tubular body 14 with the other hand, at point E for instance, and insert another portion of said tubular body, at point D for instance, into deformed slot 203. Alternatively, the surgeon may grasp pledget handle 201 with a forceps, and with the other hand grasp tubular body 14, at point E for instance. Then, while sliding tubular body 14 against access ramp 205 and towards opening of slot 203, a portion of tubular body 14 is laterally inserted within slot 203. The lateral force applied by the surgeon to insert tubular body within slot 203 may cause slot 203 to open slightly during said insertion. However, when a portion of tubular body 14 is sufficiently inserted within said slot 203, said lateral force is no longer applied. At this point, slot 203 tends to resume its biased-closed configuration, and engaged portion 147 of tubular body 14 is frictionally engaged within pledget 20.

Figure 6:
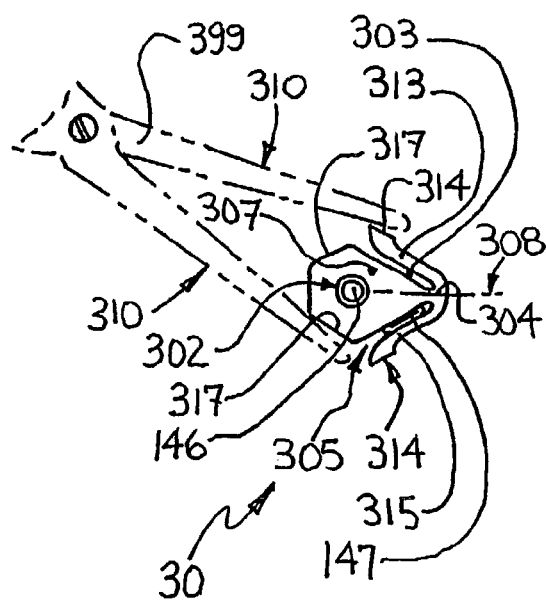
FIG. 6 is a top view illustrating a surgical loop comprising a tubular body and cooperating pledget with toggle-type bias according to a third embodiment of the present invention.

With reference to FIG. 6, a third embodiment of a surgical loop 3 is comprised of a pledget 30, a needle 12, and a substantially tubular body 14. Needle 12 and tubular body 14 are the same as those described in the first embodiment, and are not illustrated in FIG. 6. In this third embodiment, pledget 30 is comprised of a closed-perimeter opening 302, two slots 303 and 305, and a toggle-type bias 304. Similar to the first and second embodiments, pledget 30 is in a first instance engaged with a portion 146 of tubular body 14 through its closed-perimeter opening 302. A second portion 147 of tubular body 14 is then inserted in either of two slots 303 or 305.

Pledget 30 is configured with a toggle-type bias 304 which maintains each of two slots in their biased-closed configurations. As in the first and second embodiments, in the biased-closed configuration each of slots 303, 305 assume an appropriate slot width, or clamping dimension, which enables a portion 147 of tubular body 14 to be frictionally engaged and restrained when said portion is inserted there within. Slot 303 is configured between arm 313 and body 307 of pledget 30. Similarly, slot 305 is configured between arm 315 and body 307 of pledget 30. Slots 303, 305 are preferably disposed in a symmetrical orientation about the long axis 308 of pledget 30. Bias 304 simultaneously defines the end of slot 303 and also the end of slot 305.

To deform slot 305 into its open configuration, a compressive force 310 is applied to slot 303. As a result, arm 313 is brought closer to pledget body 307 while arm 317 is simultaneously moved away from pledget body 307. In order for slot 305 to assume its open configuration, slot 303 is compressed beyond its biased-closed configuration, up to a point when arm 313 comes into contact with pledget body 307. Said compressive force is preferably applied by the jaws of a forceps 399, or other like surgical implement. One said jaw is placed into contact with the ending most portion of arm 313 while the other cooperating jaw is placed into contact with lateral face 317 of pledget 30. Ending-most portion of arm 313 is preferably configured with a substantially flat surface 314, which is substantially parallel to lateral face 317 of pledget 30. Surface 314 and lateral face 317 may also be provided with a rough texture to encourage slip-free engagement with the jaws of forceps 399. Bias 304 tends to act as a toggle since as either one of slots 303, 305 is compressed or actuated beyond its biased-closed configuration, the other one of slots 305, 303 is deformed into its open configuration. Toggle-type bias 304 is configured as a substantially resilient beam or hinge and is generally the most flexible portion of pledget 30 in order to achieve the simultaneous closing of one slot and opening of other slot. In this third embodiment, either slot 303, 305 may serve to engage a portion 147 of tubular body 14.

With reference to FIG. 7A to 7C, a fourth embodiment of a surgical loop 4 is comprised of a pledget 40, a needle 12, and a substantially tubular body 14. Needle 12 and tubular body 14 are the same as those described in the first embodiment. In this fourth embodiment, pledget 40 is comprised of a handle 401, a closed-perimeter opening 402, and a substantially non-deformable slot 403. Similar to the first, second and third embodiments, pledget 40 is in a first instance engaged with a portion 146 of tubular body 14 through closed-perimeter opening 402. A second portion 147 of tubular body 14 is then inserted into slot 403.

Pledget 40 is preferably manufactured from a substantially non-deformable polymeric material, approved for surgical use. Pledget 40 is substantially elongate in shape, with a fence 406 disposed along non-contact surface 408 of pledget 40. Fence 406 preferably assumes a substantially perpendicular orientation relative to the longitudinal axis of pledget 40, and a substantially parallel orientation relative to longitudinal axis of anatomic conduit AC when said pledget 40 is fully deployed. Fence 406 protrudes from non-contact surface 408 a sufficient amount, such that a slot 403 of sufficient depth to engage a sufficient width of tubular body 14, may be configured therewithin. Alternatively, a thicker pledget 40, at least as thick as the protrusion of fence 406, may be used. This results in a pledget with a substantially flat non-contact surface 408 that is interrupted by opening 402 and slot 403. Slot 403 is configured with a chamfer 405 that spans along the open end of slot 403. An external occluder such as for example protruding ridge 417 is provided extending away from contact surface 409. Ridge 417 is similar to ridge 206 of the second embodiment, and is disposed over at least a portion of pledget body 407, between opening 402 and slot 403. Two bell-mouth notches 404 are disposed extending along the thickness of pledget body 407 and fence 406. These said bell-mouth notches tend to facilitate the insertion of portion 147 of tubular body 14 into slot 403 by laterally entrapping tubular body 14 along perimeter 418 of pledget 40.

In this fourth embodiment, portion 147 of tubular body 14 is engaged by a wedging action once tubular body 14 has partially encircled anatomic conduit AC. Said wedging action is achieved by pulling on tubular body 14 in a transverse direction that is generally parallel to the longitudinal axis of slot 403. Pulling on tubular body 14 with progressively greater force will stretch tubular body 14 thereby placing it deeper into slot 403 until it is restrainably engaged. Once portion 147 of tubular body 14 is engaged in slot 403, if more constriction of anatomic conduit is desired, the surgeon will apply a pulling force on tubular body 14, at point E for instance, while grasping pledget 40 at handle 401. Once said pulling force is sufficient to overcome friction between portion 147 of tubular body 14 and slot 403, tubular body 14 slides through said slot. As a result, the length of tubular body 14 partially encircling anatomic conduit AC between engaged portions at opening 402 and slot 403, is shortened and a larger compressive load is applied to anatomic conduit AC. In this fourth embodiment, the longitudinal axis through tubular body 14 at engaged portion 146 is substantially perpendicular to longitudinal axis through engaged portion 147.

FIGS. 8A to 8D illustrate several variants of a pledget with substantially non-deformable slot, according to the present invention. FIG. 8A illustrates a pledget 50 with a substantially S-shaped configuration, disposing two independent substantially non-deformable slots 503, and a handle 501. FIG. 8B illustrates a pledget 60 that is configured with a single common bell-mouth entrance 604, a handle 601, and a pair of opposed C-shape slots 603. FIG. 8C illustrates a substantially U-shaped pledget 70 with a common slot 703 which engages with both portions 146 and 147 of tubular body 14. FIG. 8D illustrates an elongate pledget 80 that is configured with a closed-perimeter opening 802 and a slot 803. In all these variants, opening 802 and slots 503, 603, 703 engage at least one portion of tubular body 14 such that the longitudinal axes of each of the engaged portions of tubular body 14 are in a substantially parallel orientation to one another.

Referring now to FIG. 9A, an anatomic conduit AC, for instance a coronary artery, is schematically illustrated. Encircling or looping about anatomic conduit AC with a substantially wire-like member 16, and subsequently pulling, in a generally opposed direction, on each of the two resulting lengths 168, 169 in a sense applies a tourniquet effect on said anatomic conduit. In order to constrict or ligate said anatomic conduit AC, a substantially 360 degree tourniquet is required. As such, wire-like member 16 forms a helical winding around said anatomic conduit AC. A shearing load tends to be applied to anatomic conduit AC by the pulling force exerted on each of resulting lengths 168, 169, as said pulling force is generally exerted at a different location along the longitudinal axis 119 of said anatomic conduit AC. This shearing load may induce a trauma, as it tends to distort or twist anatomic conduit AC into a tortuous configuration relative to its normal anatomic orientation. This effect is illustrated in FIG. 9B, and is especially prevalent when the diameter of anatomic conduit AC is small and approaches the external dimension of wire-like member 16. This said distortion or twisting is best illustrated by observing the longitudinal axis 119 of said anatomic conduit AC, which is substantially linear in FIG. 9A and substantially S-shaped in FIG. 9B.

Referring now to FIG. 9C, the effect of constricting or ligating an anatomic conduit AC with a surgical loop, indicated generally as 8, according to the present invention is illustrated. Anatomic conduit AC is partially encircled by a length of tubular body 14 between engaged portions 146, 147, referred to as the constricting segment 150. Simultaneously, the anatomic conduit AC is in contact with the portion of pledget 80 that generally spans between opening 802 and slot 803, and is referred to as the compressing portion 850. Compressing portion 850 is engaged with constricting segment 150 to form a complete periphery of substantial contact around said anatomic conduit. Constricting segment 150 and compressing portion 850 cooperate to apply compressive loads on anatomic conduit AC, thereby achieving the desired amount of constriction. These compressive loads are applied in a substantial plane which is oriented substantially normal to longitudinal axis 119 of said conduit. As such, a constriction of anatomic conduit AC tends to result without a shearing or twisting of said conduit relative to its normal anatomic orientation. Longitudinal axis 119 tends to remain substantially linear throughout the range of constriction or ligation applied by surgical loop 8 to said anatomic conduit AC.

Surgery performed on an anatomic conduit may at times require the use of a surgical tool, that in a sense, may also serve as an anchoring platform to substantially secure a surgical wire, during at least a part of a surgical intervention. Anchoring platforms may exist in many varieties, shapes, and sizes depending generally on their function during a surgical intervention. One variety of anchoring platform is a body tissue stabilizer. One type of tissue stabilizer, commonly referred to as a coronary artery stabilizer, may be employed to locally immobilize a portion of a patient's beating heart surface, or myocardium, in order to facilitate a surgical intervention on a coronary artery thereof, while the rest of the patient's myocardium continues to beat.

Referring now to FIGS. 10A and 11A, a coronary artery stabilizer is indicated generally as 9. Coronary artery stabilizer 9 is similar to the one described in above referenced International Application No. PCT/CA98/00821. Coronary stabilizer 9 has a body-contacting member, in the nature of a bi-furcated hand 90 for engaging a body part of a surgical patient, such as a heart, and a shaft 91. Only a portion of shaft 91 is illustrated in FIGS. 10A and 11A, that is, the portion closest to bi-furcated hand 90. As illustrated, shaft 91 is rigidly connected to hand 90. Alternatively, shaft 91 may be pivotingly connected to hand 90 through a ball and socket joint, which may be rendered rigid through an actuation member which fixes the relative position of said ball and socket. Such ball and socket joints exist in numerous varieties and are well known in the art. Shaft 91 is engageable in a positioning means which is generally comprised of one or more articulation members. One such positioning means is illustrated and described in above referenced International Application No. PCT/CA98/00821. The positioning means is in turn connectable or engaged with a substantially-stable, surgical support such as a surgical retractor, surgical table, or other like structure. The positioning means allows a surgeon or assistant to place and secure a coronary stabilizer 9 relative to said surgical support, in a desired position or orientation to the patient's heart within a surgical workspace. As such, coronary stabilizer 9 provides a mechanical force to substantially immobilize a portion of the patient's beating heart.

Hand 90 has body-contacting portions in the nature of a pair of fingers 928 and 930 joined by a yoke 932, the fingers defining between them a conduit window, or arterial window indicated generally as 934. Although fingers 928 and 930 are parallel, this is not a necessary condition for defining an arterial window. An arterial window can have two, three, or four sides, or more, or can be defined by an oval, circular, elliptical or other shaped opening, whether having a closed periphery, or a periphery open at one or more sides. For instance, a coronary stabilizer may be comprised of two, or more, mating and demountable parts which form a substantially rectangular body-contact surface within which is a substantially rectangular arterial window. Fingers 928 and 930 are for placement to either side of an anatomic conduit, such as target coronary artery TA, with longitudinal axis 919 of target artery TA substantially aligned with the notional centerline 936 of arterial window 934.

Yoke 932 has a root portion 938 attached to shaft 91, and a bent, stepped portion 940 joining root portion 938 to the proximal ends of fingers 928 and 930. Root portion 938 is substantially offset from fingers 928, 930 in height away from contacted body tissue, in this case myocardium tissue MYO, to avoid pressing down on and occluding the target artery TA which is straddled by fingers 928, 930. U-shape cut out 952 is deep enough in stepped portion 940 to clear target artery TA straddled by said fingers. Fingers 928 and 930 are sometimes referred to as ski-like, in reference to their rounded distal tips 942 and 944 that are bent to stand away from the body contacted surface in use. Each of the fingers 928 and 930 has a first, or body contacting surface 947, facing into the page in FIGS. 10A and 11A, and a second, non-contacting, exposed surface 946 for facing away from the body contacted surface while in use.

As illustrated, an array of surgical wire attachment fittings, in the nature of upstanding posts 948 are mounted to extend outwardly from surface 946. Each post has at least one slot 950 for receiving therein a wire-like member, or surgical wire such as elastomeric tubular body 17. As illustrated, each of the four slots 950 are preferably angled with respect to centerline 936 of arterial window 934. Slots 950 are wide enough to admit a stretched portion of tubular body 17, but when the stretching load is relieved, the engaged portion 179 of tubular body 17 expands and is captured in the slot. Variations in surgical wire attachment fittings are also possible. For instance, a clip-type, a spring-type, a slotted-hemisphere-type, or a plate-like-type attachment fittings, all serving to engage a portion of a surgical wire at a location extending proudly away in height away from body contact surface 947.

When tubular body 17 is anchored between two slots 950, a modest pull on an exposed end 178, in a direction generally away from arterial window 934, may increase the tension in the portion of tubular body 17 between said two slots, and adjust its position relative to slot 950. Alternatively, a modest pull in the opposite direction, generally towards arterial window 934, can decrease the tension in said portion of tubular body 17 and readjust its position relative to slot 950. As illustrated, coronary stabilizer 9 has two pairs of slotted posts 948. As such, one tubular body 17 (shown) may be placed about target artery TA, in a location upstream of an intended surgical intervention, such as arteriotomy incision 999. Similarly, another such tubular body (not shown) may be placed about target artery TA, in a location downstream of arteriotomy incision 999. This arrangement permits surgical wires to be secured on opposite sides of arterial window 934. Alternatively, other types of looping around a target artery TA may also be possible. For instance, both exposed ends 178 of tubular body 17 may be engaged in a same slot 950. In another example, one exposed end 178 is engaged in one slot 950 upstream of arteriotomy incision 999, while the other exposed end 178 is engaged in another slot 950 that is situated opposite arterial window 934, and downstream of arteriotomy incision 999.

In some instances, especially for a deep intramyocardial coronary artery, it may be desirable to want to extrude a portion of target artery TA through arterial window 934, in order to obtain better access and exposure to said target artery during a surgical intervention. When a length of tubular body 17 is placed under a target artery TA, and subsequently secured to slots 950, it tends to urge a portion of target artery TA to stand proudly in arterial window 934, since said slots are located at a height above body-contacting surfaces 947.

FIGS. 10B to 10D illustrate the effect of engaging a tubular body 17 in slotted posts 948, after it has looped around a target artery. FIG. 10B illustrates tubular body 17, at least partially encircling target artery TA, prior to the application of a tensile load on said tubular body, and prior to engaging said tubular body in slotted posts 948. One may observe that the contacted myocardium surface, containing substantially therein a target artery TA, is substantially flush with the body contact surfaces 947 of fingers 928, 930. A slight extrusion, labelled H1, is mostly due to the pressure applied by said fingers on the underlying myocardium which tends to extrude said myocardium tissue through arterial window 934. The target artery lumen cross-sectional area is essentially the unconstrained anatomic area, and is labeled A1. Referring next to FIG. 10C, a tensile load is applied to tubular body 17, and maintained by anchoring each of exposed ends 178 of said tubular body 17 in slotted posts 948, preferably located on opposite sides of arterial window 934. Based on this first tensile load applied, a portion of myocardium tissue and target artery contained substantially therein, is extruded an amount H2 through arterial window 934. Lumen area A1 is reduced to an area A2, based on the resulting compressive load that constricts target artery by virtue of applying this first tensile load. Referring next to FIG. 10D, further increasing the tensile load by pulling one or both of the exposed ends 178 through their respective slotted posts 948, will tend to further increase the amount of extrusion to H3, and further reduce the lumen area to A3. Generally in this configuration, the greater the amount of myocardium extrusion desired through the arterial window, the greater the magnitude of the resulting constriction of the target artery contained in said myocardium. In certain instances, this may induce trauma to the target artery by virtue of extensive external snaring. At times, a surgeon may desire more extrusion, but not at the expense of greater target artery constriction.

FIGS. 11B to 11D illustrate a surgical apparatus 100 according to the present invention comprising a surgical loop, indicated generally as 8, and an anchoring platform in the nature of coronary artery stabilizer 9. Although specific reference is made to a surgical loop 8, other surgical loops such as those described in previous embodiments above, may also be used.

Referring to FIG. 11B, a length of tubular body 14 is threaded through myocardium tissue that is straddled by fingers 928, 930, in a manner to at least partially encircle target artery TA substantially contained within said myocardium tissue. Pledget 80 is frictionally engaged with portion 146 of tubular body 14 through its opening 802. The contacted myocardium surface MYO is substantially flush with the body contact surfaces 947 of fingers 928,930. A slight extrusion, labelled H1, is mostly due to the pressure applied by said fingers on the underlying myocardium tissue which tends to extrude said myocardium tissue through arterial window 934. The target artery lumen cross-sectional area is essentially the unconstrained anatomic area, and is labeled A1. Referring next to FIG. 11C, portion 147 of tubular body 14 is engaged in slot 803. Target artery TA is constricted a desired amount by the cooperation of tubular body constricting length 150 and pledget compressing portion 850, in a manner as described with reference to FIG. 9C above. Lumen area A1 is reduced to an area A2. Extrusion H1 is substantially unaffected by the constriction of target artery TA. Referring next to FIG. 11D, a post-engaging portion 148 of tubular body 14, located between free end 142 and pledget-engaging portion 146, is secured in a slotted post 948. Another post-engaging portion 149, located between needle-bearing end 143 and pledget-engaging portion 147, is secured to another slotted post 948, located on the opposite side of arterial window 934. The resultant tension in each of segments 151, 152 of tubular body 14 between their respective post-engaged portions 148, 149 and pledget-engaged portion 146, 147, entrains a myocardium extrusion H2. The friction force between opening 802 and pledget-engaged portion 146, and between slot 803 and pledget-engaged portion 147 is sufficient such that the extrusion-entraining tension does not cause constricting length 150 to shorten. Referring lastly to FIG. 11E, a further increase in extrusion-entraining tension tends to cause a further increase in myocardium extrusion from an amount H2 to a larger amount H3. Lumen area A2 remains substantially preserved as the amount of extrusion increases from H2 to H3. The effect of surgical apparatus 100 on the constriction of target artery TA is illustrated. One may observe that for a given desired myocardium extrusion H3, lumen cross-sectional area is substantially maintained at a desired value of A2, as illustrated in FIG. 11E, while lumen cross-sectional area is constricted to a smaller area A3, as illustrated in FIG. 10D.

The person skilled in the art will recognize that other various pledget types according to the present invention (for instance those illustrated in FIGS. 3D, 5A, 6, 8A, 8B) may also be used, if desired, in conjunction with a coronary stabilizer in a similar manner as described above.

In deploying surgical apparatus 100, coronary stabilizer 9 serves to immobilize a portion of the patient's beating heart surface, or myocardium, relative to the remaining heart surface which is still substantially free to continue beating. A surgical loop 8 secured to attachment fittings of coronary stabilizer 9, in a manner described above, tends to isolate a target artery relative to the immobilized portion of myocardium, and tends to extrude it within the arterial window of said coronary stabilizer. Furthermore, a surgical loop 8 looped about a target artery, in a manner described above, serves to restrict blood flow through said target artery by controlling the amount of constriction or ligation, independently of the desired myocardium extrusion.

Other types of coronary artery stabilizers; that are provided with a means of engaging a surgical wire such as tubular body 14, may also be used without departing from the spirit of the present invention. For instance, a coronary stabilizer which engages the contacted body tissue, or myocardium, through a negative pressure suction force may also be used if configured with an array of surgical wire attachment fittings, such as those described above. Alternatively, a coronary stabilizer disposed with an array of clasping members or mechanical jaws or other like members capable of securing a surgical wire may also be used without departing from the spirit of the present invention.

In broad terms, a surgical procedure for the use and deployment of a surgical apparatus 100 used during a coronary artery revascularization performed on a beating heart, and relating to the present invention, preferably consists of:

(a) Performing a partial or midline sternotomy incision;
(b) Cauterizing any bleeding vessels subsequent to the sternotomy incision;
(c) Retracting the patient's ribcage through the deployment of a chest retractor;
(d) Harvesting the required number and type of suitable bypass conduits such as saphenous vein, radial artery, or internal thoracic artery to be used in the revascularization of the target coronary artery;
(e) Incising the pericardium tissue that envelopes the beating heart to expose at least a portion of the underlying myocardium surface in the general vicinity of the target artery;
(f) Positioning and orienting of the beating heart within retracted chest cavity, in order to improve surgical access to a portion of myocardium containing substantially therein a target coronary artery;
(g) Positioning and orienting of coronary stabilizer 9 with respect to the portion of myocardium containing substantially therein a target coronary artery;
(h) Securing of coronary stabilizer 9 in the desired position and orientation relative to the chest retractor through its engagement in a positioning means which is itself engaged with said chest retractor;
(i) Within arterial window 934, inserting needle 12 of surgical loop 8 into the myocardium tissue, and threading through said myocardium tissue a length of tubular body 14 (between needle bearing end 143 to pledget-engaged portion 146), in a manner to at least partially encircle a target artery contained substantially within said myocardium tissue, and at a location upstream of intended arteriotomy incision;
(j) Engaging pledget-engaging portion 147 of tubular body 14 into slot 803 of pledget 80, such that the resulting tubular body constricting length 150 and cooperating pledget compressing portion 850 apply the desired constriction to the target artery in order to restrict blood flow therein;
(k) If required, readjusting the target artery constriction by grasping pledget 80 and simultaneously pulling tubular body 14 through slot 803 in a manner to shorten or lengthen constricting length 150;
(l) Applying a tension on each segments 151, 152 of tubular body 14 and securing each of said segments into a different slotted post 948, said posts located on opposite sides of arterial window 934, in a manner to obtain a desired extrusion of myocardium tissue and target artery contained substantially therein;
(m) If desired, readjusting the amount of myocardium extrusion by pulling tubular body 14 through each of or either of the slotted posts 948 it is engaged with, in a manner that either of or each of segments 151 and 152 are shortened or lengthened;
(n) Similarly, if preferred, engaging another surgical loop 8 in a location downstream of intended arteriotomy incision, and securing it to two slotted posts 948, on opposite sides of arterial window 934;
(o) Performing a surgical intervention on target artery such as for example an arteriotomy incision;
(p) Performing a subsequent surgical intervention on target artery such as for example a bypass graft anastomosis between said target artery and said previously-harvested bypass conduit;
(q) Disengaging post-engaging portion 149 of tubular body 14 from a slotted post 948 and subsequently pledget-engaging portion 147 from slot 803 in order to substantially relieve imposed constriction on target artery;
(r) Verifying leakage at bypass graft anastomosis site;
(s) Verifying blood flow and patency through newly-grafted bypass conduit, for instance with Doppler ultrasonography;

(t) Once bypass graft is deemed surgically acceptable, disengaging surgical loop(s) entirely from myocardium tissue, and disengaging coronary stabilizer 9 from the surface of the beating heart;

(u) In multivessel coronary artery bypass graft surgeries, repeat steps (f) to (t) above for other target coronary arteries requiring a bypass graft, or coronary artery revascularization;

(v) Draining chest cavity and closing surgical patient as per standard protocol.

The concepts and principles described herein are preferably applied to a surgical loop comprising a hollow elastomeric tubular body, with a sealed lumen. Those skilled in the art will appreciate that the concepts and principles of the present invention may also apply to other types of surgical loops comprising of a hollow tubular body with unsealed lumen, a thick-walled tubular body, or a non-hollow wire-like body, or other like surgical wires.

The pledgets according to the present invention may be color-coded to reflect a classified length of tubular body, or classified needle configuration, or any other classified characteristic pertaining to a specific configuration of surgical loop. This tends to allow quicker and easier identification of a required surgical loop by the surgeon or surgical staff.

The above description of the embodiments of the present invention should not be interpreted in any limiting manner since variations and refinements are possible without departing from the spirit of the invention.

The invention claimed is:

1. A surgical attachment device for use in constricting anatomical tissue, comprising:
    an elongated wire-like member having a length extending along a longitudinal axis and including a first portion spaced apart from a second portion along the length, said elongated wire-like member further including a cross-sectional profile capable of varying between a free state cross-sectional dimension and a constrained state cross-sectional dimension, said constrained state cross-sectional dimension being smaller than said free state cross-sectional dimension; and
    a holding device engaged with said first portion of said wire-like member, and provided with a clamping member including first and second wire contact portions defining a wire-like member receiving space therebetween, said holding device including a lateral opening communicating with said space and communicating with the outside environment such that a segment of said wire-like member may be inserted from the outside environment into said space by moving said wire-like member through the lateral opening in a direction transverse to said longitudinal axis, at least one of said first and second wire contact portions movable with respect to the other of said first and second wire contact portions between a biased-closed configuration and an open configuration, said holding device further including a resilient element configured to receive a compression force to move said clamping member to said open configuration wherein under the compression force in said open configuration said first and second wire contact portions are spaced by a distance greater than said free state cross-sectional dimension and in said biased-closed configuration said first and second wire contact portions are biased together by said resilient element into said biased-closed configuration to engage and hold said second portion of said wire-like member in said constrained state cross-sectional dimension.

2. A surgical attachment device according to claim 1, wherein said compression force is applicable in a direction that is generally orthogonal to a longitudinal axis of said second portion of said wire-like member.

3. A surgical attachment device according to claim 2, wherein said holding device is elongate and said compression force is applicable in a direction that is generally orthogonal to both said longitudinal axis of said second portion of said wire-like member and to a longitudinal axis of said holding device.

4. A surgical attachment device according to any one of the preceding claims, wherein said first and second wire contact portions are configured to form an elongate slot.

5. A surgical attachment device according to claim 4, further comprising an actuator adapted to move at least one of said wire contact portions between said biased-closed configuration and said open configuration when actuated, said actuator including a pair of separated elements that may be compressed toward each other under the compression force.

6. A surgical attachment device according to claim 4, wherein said holding device further comprises an attachment member for engaging said first portion of said wire-like member, said attachment member adapted to simultaneously provide:
    a sliding engagement of said first portion of said wire-like member through said holding device; and
    a restraining force acting on said first portion of said wire-like member by altering the cross section profile of said first portion from a free state cross section profile to a different constrained state cross section profile.

7. A surgical attachment device according to claim 6, wherein said attachment member includes a closed perimeter opening.

8. A surgical attachment device according to claim 6, wherein said attachment member includes an open slot.

9. A surgical attachment device according to claim 4, wherein said first and second wire contact portions are provided at a free end of said holding device.

10. A surgical attachment device according to claim 5, wherein said resilient element further comprises a resilient hinge connecting said first and second wire contact portions and disposed between said clamping member and said actuator.

11. A surgical attachment device according to claim 10, wherein a longitudinal axis of said first portion of said wire-like member is substantially parallel to an axis of said resilient hinge.

12. A surgical attachment device according to claim 5, further comprising a second clamping member thereby providing a pair of clamping members, said pair of clamping members being substantially symmetrically arranged and extending from a resilient common hinge and each one of said clamping members serving as an actuator for the other.

13. A surgical attachment device according to claim 5, wherein said first and second wire contact portions are provided at a substantially central portion of said holding device and said actuator is provided at a free end thereof.

14. A surgical attachment device according to claim 5, wherein said holding device is unitary.

15. A surgical attachment device according to claim 5, wherein at least one of said wire contact portions of said clamping member cooperates with a spring member.

16. A surgical attachment device according to claim 5, wherein at least a portion of said actuator cooperates with a spring member.

17. A surgical attachment device according to claim 5, wherein at least one of said wire contact portions of said clamping member is provided with a friction-enhancing texture.

18. A surgical attachment device according to claim 5, wherein said clamping member is comprised of a plurality of wire contact portions disposed in a saw-tooth like configuration.

19. A surgical attachment device according to claim 1, wherein said wire-like member extends between a first end and a second end, and wherein said first end is provided with a tissue-piercing member.

20. A surgical attachment device according to claim 19, wherein said second end is configured with an enlarged ending portion.

21. A surgical attachment device according to claim 1, wherein said wire-like member is an elastomeric wire.

22. A surgical attachment device according to claim 21, wherein said elastomeric wire has a hollow substantially central portion.

23. A surgical attachment device according to claim 1, wherein, in use, the resulting length of said wire-like member spanning between said engaged first portion and said engaged second portion cooperates with at least a portion of said holding device to ligate anatomic tissue contained therewithin.

24. A surgical attachment device according to claim 1, wherein said resilient element is positioned between said clamping member and a portion of said holding device which is more resistant to compression than said resilient element.

25. A surgical attachment device according to claim 24, wherein said resilient element further comprises a pair of spaced apart deformable portions of said holding device.

26. A surgical attachment device according to claim 25, further comprising an opening disposed between said spaced apart deformable portions.

27. A surgical attachment device according to claim 25, wherein said spaced apart deformable portions further comprise spaced apart rails.

28. A surgical attachment device according to claim 1, wherein said resilient element further comprises a pair of spaced apart deformable portions of said holding device.

29. A surgical attachment device according to claim 28, further comprising an opening disposed between said spaced apart deformable portions.

30. A surgical attachment device according to claim 28, wherein said spaced apart deformable portions further comprise spaced apart rails.

31. A surgical attachment device for use in constricting anatomical tissue, comprising:
an elongated wire-like member having a length extending along a longitudinal axis and including a first portion spaced apart from a second portion along the length, said elongated wire-like member further including a cross-sectional profile capable of varying between a free state cross-sectional dimension and a constrained state cross-sectional dimension, said constrained state cross-sectional dimension being smaller than said free state cross-sectional dimension; and
a holding device engaged with said first portion of said wire-like member, and provided with a clamping member including first and second wire contact portions defining a wire-like member receiving space therebetween, said holding device including a lateral opening communicating with said space and communicating with the outside environment such that a segment of said wire-like member may be inserted from the outside environment into said space by moving said wire-like member through the lateral opening in a direction transverse to said longitudinal axis, at least one of said first and second wire contact portions movable with respect to the other of said first and second wire contact portions between a biased-closed configuration and an open configuration, said holding device further including a resilient element configured to receive a compression force to move said clamping member to said open configuration wherein under the compression force in said open configuration said first and second wire contact portions are spaced by a distance greater than said free state cross-sectional dimension and in said biased-closed configuration said first and second wire contact portions are biased together by said resilient element into said biased-closed configuration to hold said second portion of said wire-like member in said constrained state cross-sectional dimension,
said holding device further including a closed-perimeter opening spaced from said wire-like member receiving space for holding a second portion of said wire-like member.

* * * * *